United States Patent [19]
Brugger et al.

[11] 3,997,271
[45] Dec. 14, 1976

[54] DEVICE FOR CALIBRATING A TRANSMISSOMETER

[76] Inventors: Richard D. Brugger, 4818 Walker Blvd., Erie, Pa. 16509; Robert H. Wager, Jr., Passaic Ave.; Richard Krukowski, 205 Washington Ave., both of Chatham, N.J. 07928

[22] Filed: Mar. 10, 1975

[21] Appl. No.: 557,030

[52] U.S. Cl. .............................. 356/201; 356/207; 356/243
[51] Int. Cl.² .................. G01N 21/22; G01N 21/12
[58] Field of Search .................. 356/201, 207, 243

[56] References Cited
UNITED STATES PATENTS

| | | | |
|---|---|---|---|
| 3,234,846 | 2/1966 | Cropper et al. | 356/243 |
| 3,702,734 | 11/1972 | Lindahl et al. | 356/207 |
| 3,850,529 | 11/1974 | Brugger | 356/207 |

*Primary Examiner*—Vincent P. McGraw

[57] ABSTRACT

This specification discloses a device for resetting the zero calibration of an opacity sensing meter (transmissometer) made up of a light source which may be located on one side of a smokestack, and a sensing element located on the other side of the smokestack. The rezeroing device will rezero the sensing element without using the light passing through the stack. The device samples the light at the source side of the stack by mechanically introducing an auxiliary light sensor, and generates an output from a mechanically introduced auxiliary source located on the sensor side of the stack such that excitation of the normal system sensor by the auxiliary source is the same as the excitation would be to the sensor by the normal source.

10 Claims, 8 Drawing Figures

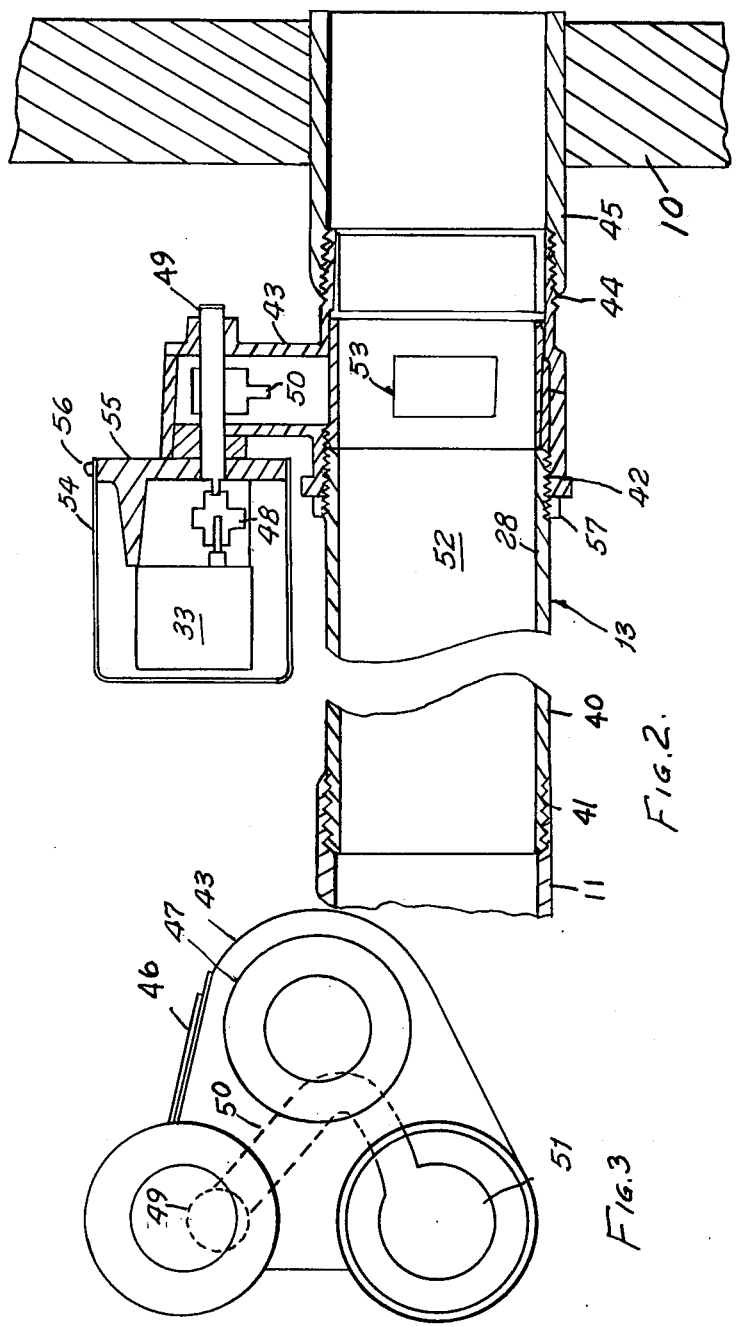

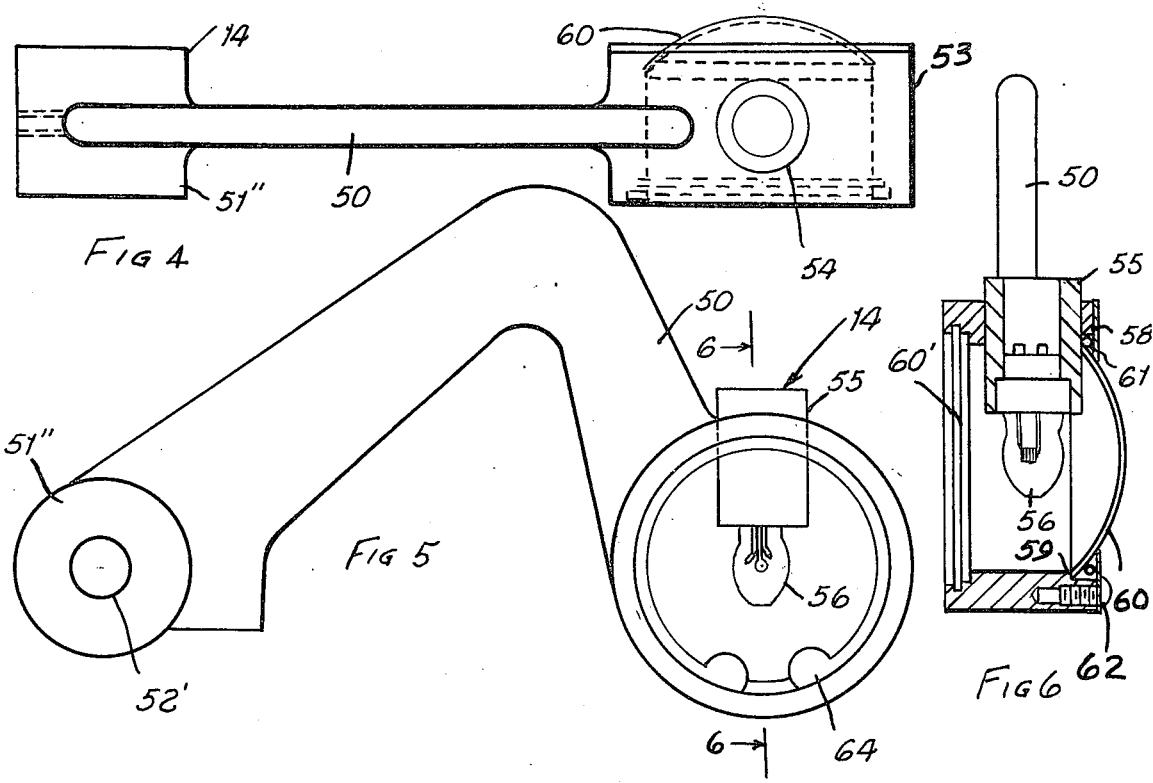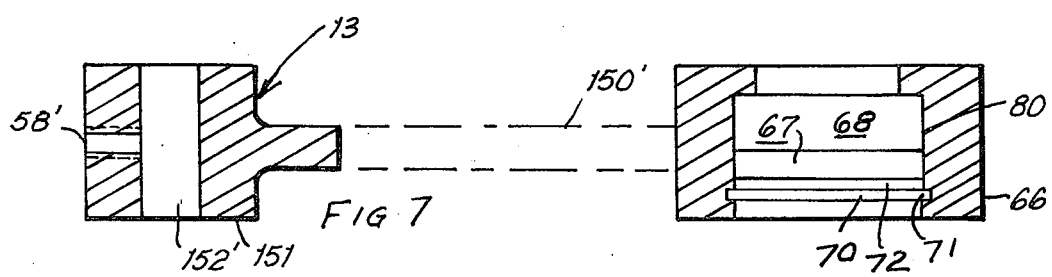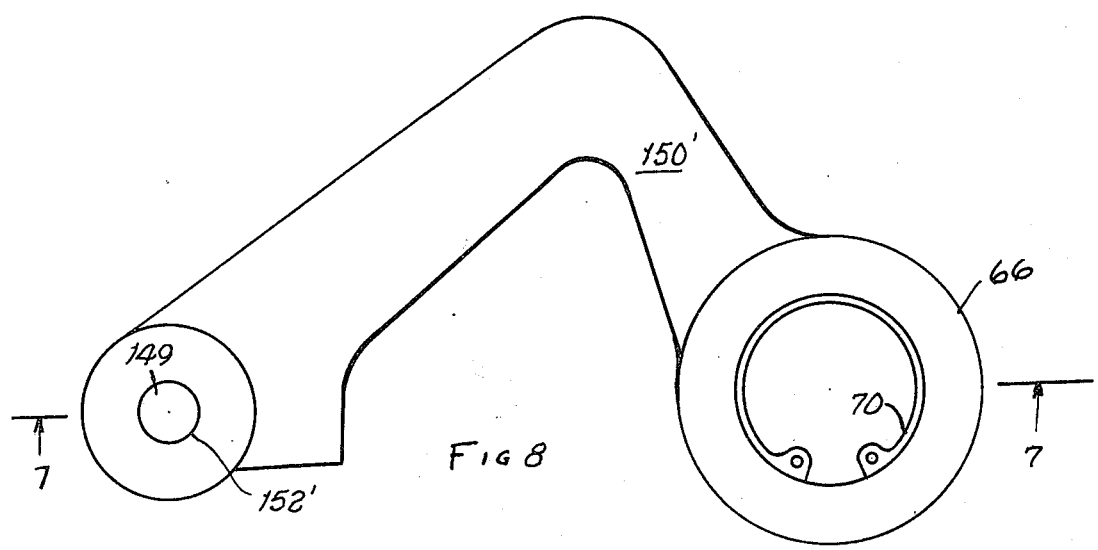

DEVICE FOR CALIBRATING A TRANSMISSOMETER

GENERAL DESCRIPTION OF INVENTION

Increased interest in the control of atmospheric pollution puts requirements on the monitoring of effluence from smokestacks. On such characteristic to be monitored is the opacity or optical density of the flue gas which is measured on a scale of neutral density, percent opacity, or by the Ringelmann Scale. Such systems are known as transmissometers. Transmissometers have a light source on one side of the stack and a sensing means on the other. The zero calibration point of the meter of the sensing means is normally set with the light on and no smoke in the stack. In practice, it is seldom that the operator has a stack with clear gas in it, with which to work. After the zero point of the transmissometer is originally set, there are factors which dictate that the meter should be rezeroed: (1) aging of lamps with resulting light output; (2) lamp replacement (each lamp does not have the same lumen output); (3) accumulation of dirt on the lenses and windows facing the stack, with subsequent reduction in the amount of light transmitted.

The means to zero calibrate the system without going through the stack, as well as to check the zero point of the opacity meter is also needed because in operating systems with certain fuels, it is not possible to get a clear gas in the stack for calibration purposes unless the entire boiler or smoke production system is out for some other reason.

REFERENCE TO PRIOR PATENTS

This patent application is an improvement on U.S. Pat. No. 3,850,529.

REFERENCE TO PRIOR ART

U.S. Pat. No. 3,376,425—Wager
U.S. Pat. No. 3,453,049—Wager
U.S. Pat. No. 3,838,925—Marks

OBJECTS OF THE INVENTION

It is an object of the invention to provide a means to externally zero a transmissometer.

Another object of the invention is to provide a means of mechanically introducing an auxiliary sensor at the source side of the stack. Output of the source, as monitored on a meter, is used to establish whether the source output is equal to the source intensity at set up. Provision is made to adjust the source intensity so that it can be returned to a value at set up.

Another object of the invention is to provide a means of mechanically introducing an auxiliary source at the sensor side of a stack. This auxiliary source is a standard established at original set up, and energized only at set up and when the system is being externally zeroed.

Still another object of the invention is to have as the primary source a Halogen-cycle/optics combination which generates a light beam of angular definition suitable to the needs of the auxiliary sensor which forms a part of this system.

With the above and other objects in view, the present invention consists of the combination and arrangement of parts hereinafter more fully described, illustrated in the accompanying drawing and more particularly pointed out in the appended claims, it being understood that changes may be made in the form, size, proportions, and minor details of construction without departing from the spirit or sacrificing any of the advantages of the invention.

GENERAL DESCRIPTION OF DRAWINGS

FIG. 2 is a cross-sectional view of the motor-driven mechanism for swinging the auxiliary source and/or sensor into the path of the normal light beam.

FIG. 3 is an end view of the device shown in FIG. 2.

FIG. 4 is a view of the arm holding the auxiliary light element.

FIG. 5 is a side view of the arm holding the auxiliary light source.

FIG. 6 is a cross-sectional view taken on line 6—6 of FIG. 5.

FIG. 7 is a cross-sectional view taken on line 7—7 of FIG. 8.

FIG. 8 is a side view of the arm supporting the auxiliary sensing element.

DETAILED DESCRIPTION OF THE DRAWINGS

Figure 1:
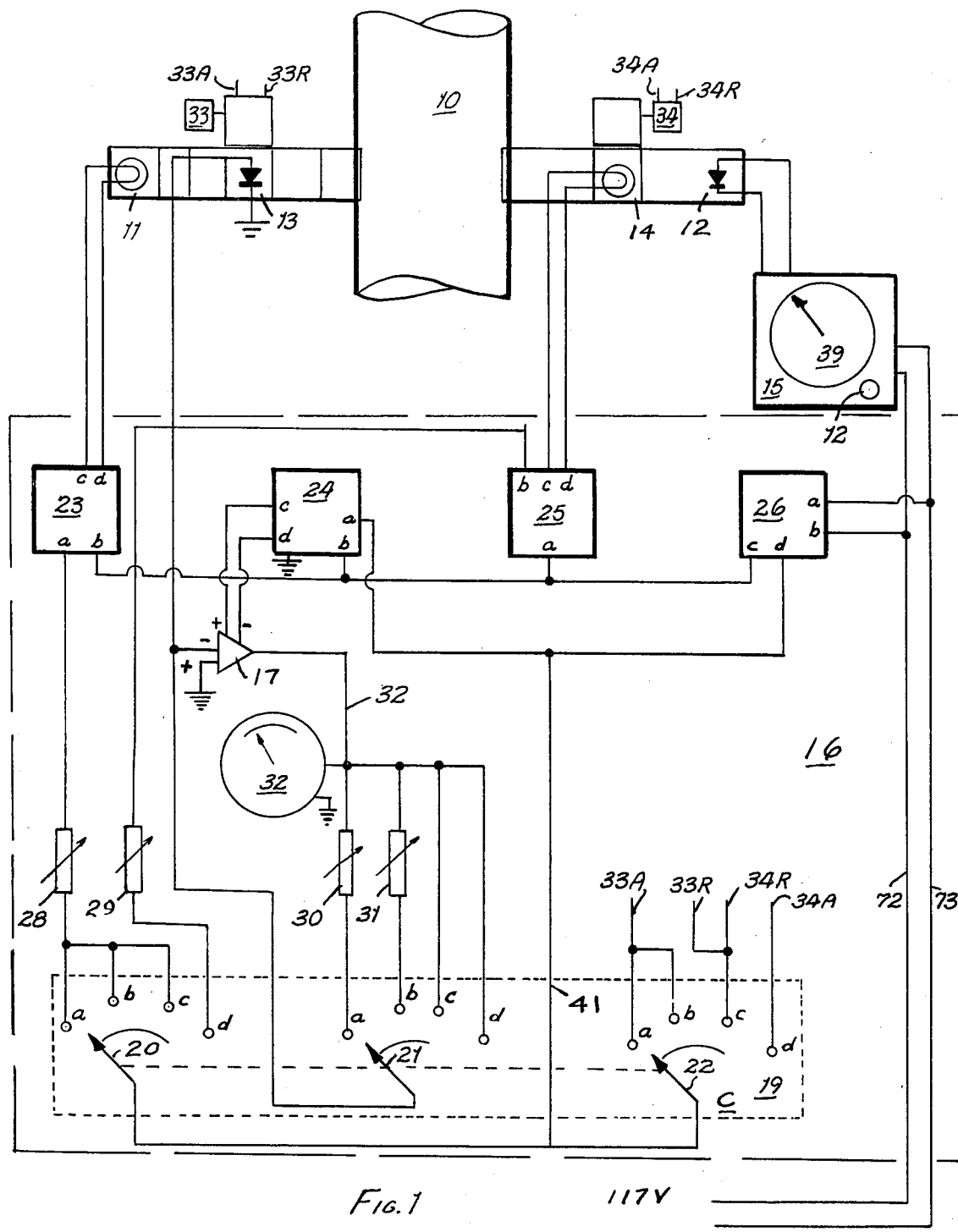
FIG. 1 shows an embodiment of a schematic diagram of the stack monitoring apparatus with its circuit diagram.

The system illustrated in the drawings herein comprises a stack 10, a normal system with a light source 11, a normal system sensor 12, an auxiliary system sensor 13, and an auxiliary light source 14, signal conditioner unit 15 (normal instrumentation for measuring transmission), and dynamic calibration unit 16.

The dynamic calibration unit 16 contains an operational amplifier 17. The performance of the operational amplifier 17 is substantially determined by the external components. Various configurations of these external components are possible. The configuration used in the preferred embodiment disclosed herein is one in which the auxiliary light sensor (photo-conductive cell 13) is connected to the negative input of the amplifier 17, such that the amplifier 17 presents a low impedance load to sensor 13; thus utilizing essentially the short circuit current output of sensor 13, which is essentially linear with regard to illumination. The short circuit current times the feedback resistor flow around the operational amplifier and is the output voltage of the circuit. The gain is established by variable potentiometer elements with different units 30, 31 switch into the circuit to bring some preset gains or adjustable gains into the system by switch 19 as the system operation may require. A gang switch 19, which is part of the dynamic calibration unit has three banks, A, B and C of fixed contacts, each bank of fixed contacts has a movable contact 20, 21 and 22 respectively.

The dynamic calibration unit also has regulated (ferro-resonant transformer) power supply 26, power supply 23 for the primary light source 11, regulated D.C. power supply 24, for the operation amplifier, and a power supply 25 for the auxiliary light source 14. Power supply 23 has a primary source intensity adjusting potentiometer 28, and power supply 25 has an auxiliary source adjusting potentiometer 29.

The arm and motor assembly of both the auxiliary sensing unit 13 and the auxiliary light source 14 are substantially identical in external structure; therefore, only the unit 13 will be described in detail. The sensing unit 13 is made up generally of a pipe nipple 40 threaded at its ends 41 and 42. The end 41 will thread into the primary light source 11 and the end 42 will threadably engage the housing 43. The housing 43 is locked to threaded end 42 by locknut 47. The housing 43 is itself externally threaded at 44 to threadably engage a sleeve 45 which fits into the stack 10, thereby providing a light path from the primary light source 11 through the stack 10 to the auxiliary light source 14 and the primary sensing unit 12. The motor 33 is connected through coupling 48 to the shaft 49, and shaft 49 is connected to the arm 50. The arm 50 is capable of swinging the auxiliary light element 50 from a position 51' out of the light path 52 to the position 51 in the light path 52. A cup shaped cover 54 is supported on the motor 55 and held in place by screw 56. Cover 46 provides access to the arm inside the housing 43 and cover 47 provides access to the device on the arm.

The arm 50 has a boss 51'' bored at 52' to receive the shaft 49. Arm 50 has a boss 53 on its opposite end bored to receive the lamp 56. Lamp 56 is supported in socket 55, reflector 60 is received in the counterbore and held in place by the flat washer 58, which holds the sealing ring 60 against the reflector and is held in place by the screw 62. A frosted glass 60 is supported on the boss by a snap ring 64.

The auxiliary sensing element 13 has an arm 150 having a boss 151 on one end bored at 152' to receive a motor shaft 149. The opposite end of arm 150 has the boss 66 bored to receive the photo cell 68, filter 67, and frosted glass 72, all held in position by the snap ring 70 which is received in the groove 71.

The lamp of the primary light source 11 is supplied from power supply 23 which is in turn powered by power supply 26. the intensity of the primary light source can be adjusted by the potentiometer 28, when the switch 19 is in the a, b, or c positions. The secondary light source 14 is supplied power by power supply 25 when the switch 19 is in the d position through auxiliary source adjusting potentiometer 29, whereby the intensity of the light source 14 can be adjusted. The auxiliary sensor 13 is connected to the negative (inverting) input to the amplifier 17 such that the amplifier 17 presents a low impedance load to the sensor thus utilizing essentially the short circuit current output of the sensor which is essentially linear with the illumination. Reference adjust potentiometers 30 and 31 can be switched into the circuit by common terminal 21 of stage B to change the gain of the amplifier.

The a and b terminals of switch 19, stage C are connected to the advanced terminal of motor 33 to move the auxiliary sensor 13 into the path of light. The c terminal of the C gang switch 19 is connected to the retract position on both the motor 33 and 34, whereby the auxiliary sensor and auxiliary light are swung out of the light path; thus, when switch 19 is in the c position, both motors 33 and 34 will retract the auxiliary sensor 13 and the auxiliary light source 14 respectively. When the switch 19 is in the d position, power from power supply 26 will be connected to the advance position of motor 34 thereby advancing the auxiliary sensing unit 14 into the light path.

The system is re-zeroed in basically two steps as the initial set up and basic calibration have been performed.

Initial calibration and normal operation are both performed with switch 19 in the c position with the auxiliary sensor 13 and the auxiliary light source 14 in a retracted position. Initial calibration is performed with no smoke in the stack 10.

Initial calibration is performed by moving switch 19 to the c position and by adjusting light source 11 by means of primary source adjustment potentiometer 28 until the opacity meter 39 reads 0 percent.

The auxiliary detector cell 13 is calibrated with switch 19 in the a position, thus advancing detector cell 13 to a position in front of the light source 11 and the gain of the amplifier is adjusted by potentiometer 30 until the meter 32 reads 95 percent. Finally, to calibrate the auxiliary source, switch 19 is moved to the d position and auxiliary source 14 is moved into the advanced position in front of the primary detector cell 12 and this intensity is adjusted by means of auxiliary source adjusting potentiometer 29 so that the output of the opacity meter 39 reads 0 percent. When the above has been properly accomplished, the primary detector 12, output with a clear stack or from the auxiliary source 14 will each cause the opacity meter 39 to read 0 percent. The output of the auxiliary cell 13 from the primary light source 11 will make meter 32 read 95 percent.

To recalibrate the primary light source 11, as when replacing bulbs, switch 19 is moved to the a position, window in front of primary light must be clean. Auxiliary sensor 13 moves to a position in front of primary light source 11 and adjust potentiometer 28 until meter 32 reads 95 percent.

After the boiler is in operation and the smoke is in the chimney 10, the primary light source 11 will produce a reading of 95 percent on the auxiliary meter 32 with the switch 19 in the b position, (unless the primary light source has degraded or the lens in front if it has become dirty, in which case the intensity of the primary light source must be adjusted by potentiometer 28 to bring the auxiliary meter 32 back to 95 percent with switch 19 in the b position. With switch 19 in the d position, the auxiliary light source, projecting light on the primary detector 12 will produce a reading of 0 percent on the opacity meter 39 (unless the lens in front of it has become dirty), in which case the signal conditioner unit 15 must be adjusted by means of control 12.

The foregoing specification sets forth the invention in its preferred practical forms but the structure is capable of modification within a range of equivalents without departing from the invention which is to be understood is broadly novel as is commensurate with the appended claims.

The embodiments of the invention in which an exclusive property or privilege is claimed are defined as follows:

1. A device for recalibrating a transmissometer having a primary light source supported on a first side of a duct and a primary detector supported on a second side of said duct and an opacity meter connected to said primary detector with a light path through said duct from said primary light source to said primary detector comprising, an auxiliary detector adapted to move into said light path and to be supported at said first side of said duct between said primary light source and said duct, an auxiliary light source having a known output, and means to move said auxiliary source into a position between said duct and said primary detector, and adjusting means connected to said opacity meter to set the said opacity meter to read a predetermined value, auxiliary meter means connected to said auxiliary detector and means to adjust said primary light source for reading of a predetermined value on said auxiliary meter means wherein the primary light source can be adjusted for proper illumination, said adjusting means connected to said primary light source being adapted to adjust the intensity of said primary light source, and said adjusting means connected to said opacity meter being adapted to adjust said opacity meter to give a reading of a predetermined value on said opacity meter, as if a clear gas were in said stack and as if said auxiliary detector and said auxiliary light source were removed from said light path.

2. The device recited in claim 1 wherein means is connected to said auxiliary light source to adjust the intensity of said auxiliary light source to cause said transmissometer to read said predetermined valve.

3. The device recited in claim 1 wherein said means to move said auxiliary lights comprises motor means provided on said device for moving said auxiliary detector means in and out of the path of light between said primary light source and said primary detector.

4. The device recited in claim 1 wherein said means for connecting said meter to said auxiliary detector comprises an operational amplifier and a first potentiometer and a second potentiometer and, means for connecting said first potentiometer means and said second potentiometer means selectively from the input of said amplifier to the output of said operational amplifier whereby the gain of said operational amplifier is controlled.

5. The device recited in claim 4 wherein an auxiliary light source, having a predetermined intensity to cause said primary detector to read said predetermined value, is between said duct and said primary detector and projecting light from said auxiliary light source onto said primary detector, to determine said predetermined value thereon.

6. The device recited in claim 2 wherein said means for moving said auxiliary sensing unit and said auxiliary light source into and out of said path of light comprises motor means.

7. The device recited in claim 6 wherein said auxiliary light source is supported on first arm means and said auxiliary detector is supported on second arm means and said motor means comprises a first motor connected to said first arm means and a second motor connected to said second arm means whereby said arm means are swung to bring said auxiliary light source and said auxiliary detector into and out of said light path.

8. The device recited in claim 1 wherein an operational amplifier is connected to said auxiliary detector connecting said auxiliary detector to an output meter and a first potentiometer and a second potentiometer are connected to said operational amplifier and adapted to be selectively connected from the output to the inverting input thereof, whereby the gain of said to the inverting input thereof, whereby the gain of said amplifier can be adjusted.

9. A method of recalibrating a transmissometer made up of a primary light source supported at the first side of a duct and a primary detector supported on the second side of said duct and an opacity meter having an adjusting means connected to said primary detector, said transmissometer and recalibrating means having been coordinated during initial installation with said primary light source, projecting light through said duct onto said primary detector with a clear gas in said duct comprising moving an auxiliary detector having a meter connected to it between said primary light source and said duct and adjusting said primary light source to give a predetermined reading on said meter, moving a secondary light source between said duct and said primary detector and adjusting said means on said opacity meter to give a predetermined value thereon, whereby said transmissometer can be recalibrated even if said duct contains dense, opaque gas.

10. The method recited in claim 9 wherein an auxiliary light source is moved between said primary detector and said duct adjusting the intensity of said auxiliary light source during initial set-up to a predetermined value and subsequently recalibrating said primary detector of said transmissometer by projecting the light from said auxiliary light source onto said primary detector and adjusting said transmissometer.

* * * * *